(12) United States Patent  
Prindiville et al.

(10) Patent No.: US 10,806,526 B2  
(45) Date of Patent: Oct. 20, 2020

(54) WRIST MECHANISM FOR SURGICAL INSTRUMENT

(71) Applicant: INTUITIVE SURGICAL OPERATIONS, INC., Sunnyvale, CA (US)

(72) Inventors: Michael Prindiville, Portola Valley, CA (US); Paren Shah, Los Gatos, CA (US)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 1240 days.

(21) Appl. No.: 15/023,336

(22) PCT Filed: Oct. 16, 2014

(86) PCT No.: PCT/US2014/060951  
§ 371 (c)(1),  
(2) Date: Mar. 18, 2016

(87) PCT Pub. No.: WO2015/057990  
PCT Pub. Date: Apr. 23, 2015

(65) Prior Publication Data  
US 2016/0228202 A1  Aug. 11, 2016

Related U.S. Application Data

(60) Provisional application No. 61/892,990, filed on Oct. 18, 2013.

(51) Int. Cl.  
*A61B 34/30* (2016.01)  
*A61B 17/29* (2006.01)  
(Continued)

(52) U.S. Cl.  
CPC ........ *A61B 34/30* (2016.02); *A61B 17/00234* (2013.01); *A61B 17/29* (2013.01);  
(Continued)

(58) Field of Classification Search  
CPC .......... A61M 25/0105; A61M 25/0141; A61M 25/0147; A61M 25/0133; A61M 25/0138;  
(Continued)

(56) References Cited

U.S. PATENT DOCUMENTS 5,797,900 A    8/1998   Madhani et al.  
6,068,250 A *   5/2000   Hawkins ................. F16F 1/328  
                                                                                   267/148  
(Continued)

FOREIGN PATENT DOCUMENTS

CN          1723835 A     1/2006  
CN          1728972 A     2/2006  
(Continued)

OTHER PUBLICATIONS

Extended European Search Report for Application No. 14854628.6, dated Apr. 3, 2017, 12 pages.  
(Continued)

*Primary Examiner* — Tiffany Legette  
(74) *Attorney, Agent, or Firm* — IP Spring

(57) ABSTRACT

A wrist mechanism for a surgical instrument is disclosed. In some implementations, a surgical instrument includes an end effector and a unitary wrist mechanism coupled to the end effector, where the wrist mechanism is formed from a single piece of material. The wrist mechanism provides at least one degree of freedom to the end effector, and includes a plurality of link members linked together as well as one or more flexures, where at least one of the flexures includes a chain of a connected plurality of segments. Each flexure connects associated adjacent link members and enables rotational movement of the associated link members relative to each other to provide an associated degree of freedom to the end effector.

19 Claims, 7 Drawing Sheets

(51) Int. Cl.
*A61B 34/00* (2016.01)
*A61B 17/00* (2006.01)

(52) U.S. Cl.
CPC .... *A61B 34/71* (2016.02); *A61B 2017/00309* (2013.01); *A61B 2017/00314* (2013.01); *A61B 2017/2927* (2013.01); *A61B 2034/305* (2016.02); *A61B 2034/306* (2016.02); *A61B 2218/001* (2013.01)

(58) Field of Classification Search
CPC .......... A61M 2025/015; A61B 1/0055; A61B 2034/305; A61B 2034/306; A61B 2017/00314; A61B 34/30; A61B 17/29; A61B 17/00234; A61B 2017/2927; A61B 34/71; A61B 2218/001
See application file for complete search history.

(56) References Cited

U.S. PATENT DOCUMENTS

| | | | |
|---|---|---|---|
| 6,817,974 | B2 | 11/2004 | Cooper et al. |
| 7,320,700 | B2 | 1/2008 | Cooper et al. |
| 7,678,117 | B2 | 3/2010 | Hinman et al. |
| 2003/0036748 | A1* | 2/2003 | Cooper ............ A61B 17/00234 606/1 |
| 2004/0044270 | A1 | 3/2004 | Barry |
| 2005/0182298 | A1 | 8/2005 | Ikeda et al. |
| 2006/0178556 | A1* | 8/2006 | Hasser ................. A61B 1/0055 600/102 |
| 2010/0123396 | A1 | 5/2010 | Devincentis et al. |
| 2011/0152879 | A1 | 6/2011 | Williams |
| 2012/0123395 | A1 | 5/2012 | Stoy et al. |
| 2012/0123396 | A1 | 5/2012 | Lutze et al. |
| 2012/0215220 | A1 | 8/2012 | Manzo et al. |
| 2013/0046317 | A1 | 2/2013 | Blumenkranz |
| 2013/0046318 | A1 | 2/2013 | Radgowski et al. |
| 2013/0046336 | A1* | 2/2013 | Blumenkranz ........ A61B 17/29 606/205 |
| 2013/0267936 | A1 | 10/2013 | Stroup et al. |

FOREIGN PATENT DOCUMENTS

| | | |
|---|---|---|
| WO | WO-2004052171 A2 | 6/2004 |
| WO | WO-2013084985 A1 | 6/2013 |

OTHER PUBLICATIONS

Haga Y et al., "Development of Minimally Invasive Medical Tools Using Laser Processing on Cylindrical Substrates," Electrical Engineering in Japan, vol. 176, No. 1, Apr. 21, 2011 (Apr. 21, 2011), pp. 65-74, XP055358433, ISSN: 0424-7760, DOI: 10.1002/eej.21030.
Sieklicki W., et al., "Superelastic Compliant Mechanisms for Needlescopic Surgical Wrists," Reconfigurable Mechanisms and Robots, 2009, REMAR 2009, ASME/IFTOMM International Conference on, IEEE, Piscataway, NJ, USA, Jun. 22, 2009 (Jun. 22, 2009), pp. 392-399, XP031496706, ISBN: 978-88-89007-37-2.
International Search Report and Written Opinion for Application No. PCT/US2014/060951, dated Jan. 26, 2015, 9 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Office Action dated Aug. 24, 2018 for Chinese Application No. 201480057356.7 filed Oct. 16, 2014; 20 pages.

* cited by examiner

WRIST MECHANISM FOR SURGICAL INSTRUMENT

RELATED APPLICATIONS

This application is the U.S. national phase of International Application No. PCT/US2014/060951 (filed Oct. 16, 2014), which designated the U.S. and claimed the benefit of U.S. Provisional Patent Application No. 61/892,990 (filed Oct. 18, 2013), the contents of each of which are incorporated herein by reference.

BACKGROUND

The present disclosure relates generally to surgical instruments and, more particularly, to wrist mechanisms for articulate surgical instruments.

Robotic surgery uses various types of medical instruments to perform minimally invasive surgical procedures that minimize damage to healthy tissue of patients. Such medical instruments may include wrist mechanisms to allow medical instruments to be remotely manipulated in different manners and directions. For example, wrist mechanisms can be used in surgical tools having end effectors such as scalpels, scissors, forceps, grasping implements, cauterizing tools, irrigation tools, suction tools, etc. The wrist mechanisms can allow such end effectors multiple ranges of motion to allow the operator to position and use the end effector effectively in the operating space. Some implementations can use actuators and transmission mechanisms such as cables to allow remote control over the motion of the end effector.

In some medical instruments, wrist mechanisms include multiple linked stages that are connected or held together and which can move relative to each other to enable motion to the attached end effector. However, the cost and assembly of such wrist mechanisms can be excessive. For example, some systems may use cables to tension and hold the multiple wrist linkage stages together, requiring precise and complex tensioning and adjusting operations to assemble.

What is needed is a wrist mechanism for a surgical instrument that provides extensive motion to surgical instrument end effectors and has reduced production and assembly costs.

SUMMARY

Implementations of the present application relate to wrist mechanisms for surgical instruments. In some implementations, a surgical instrument includes an end effector and a unitary wrist mechanism coupled to the end effector, where the wrist mechanism is formed from a single piece of material. The wrist mechanism provides at least one degree of freedom to the end effector, and includes a plurality of link members linked together, as well as one or more flexures. At least one of the flexures includes a chain of a connected plurality of segments. Each flexure connects associated adjacent link members and enables rotational movement of the associated link members relative to each other to provide an associated degree of freedom to the end effector.

One or more implementations can provide additional features. For example, each link member can annular and approximately cylindrical in shape. The link members can be serially linked, and each longitudinal axis of each cylindrical link member can be approximately aligned in an unflexed state of the one or more flexures. The wrist mechanism can provide at least two degrees of freedom to the end effector, where a first one of the degrees of freedom is about a pitch axis and a second one of the degrees of freedom is about a yaw axis that is nonparallel to the pitch axis and is nonparallel to a longitudinal axis extending through the wrist mechanism. Each of the associated link members can have a tapered end portion tapered in a direction away from the connected link member to allow the rotational motion between the associated link members. Each link member can be connected to at least one of the other link members by at least one of the flexures. Each of the flexures can be coupled between opposing end sides of two associated cylindrical link members. Each of the flexures can enable relative rotational movement between the associated link members about a rotational axis extending approximately perpendicularly to a longitudinal axis extending through at least one of the associated link members.

Each of the one or more flexures can provide a spring force to the associated link members connected by the flexure. The plurality of segments can include linear segments connected in an S-pattern. For example, two flexures can connect two of the link members on approximately opposite sides of a longitudinal axis of each of the cylindrical link members. The wrist mechanism can include at least one stop member coupled to a link member between associated adjacent link members, where the stop member prevents the rotational motion between the associated link members beyond a predetermined angular range. For example, the stop member can be provided on one link member and can engage a receiving recess in the opposing side end of the associated link member in response to the link members being rotated by a predetermined amount with respect to each other.

The surgical instrument can further include a force transmission element coupled to the wrist mechanism to enable actively moving the end effector by rotating at least one link member in the at least one degree of freedom, and an actuator coupled to the force transmission element. For example, the force transmission element can include one or more cables and/or guides for the cables. The surgical instrument can further include a shaft coupled to the wrist mechanism. Some implementations can include a tube extending down the shaft, through the wrist mechanism, and to the end effector, where the tube provides a passage for material to be moved to or from the end effector.

In some implementations, a wrist mechanism for a surgical instrument includes a plurality of link members linked together, and one or more flexures. At least one of the flexures includes a chain of a connected plurality of segments. Each flexure connects associated adjacent link members and enables rotational movement of the associated link members relative to each other to provide an associated degree of freedom to the end effector. The link members and flexures are formed from a single piece of material, and the wrist mechanism provides at least one degree of freedom between the ends of the wrist mechanism. In some implementations, each link member can be annular and approximately cylindrical, and each of the flexures can enable relative rotational movement between the associated link members about a rotational axis extending approximately perpendicularly to a longitudinal axis extending through at least one of the associated link members. Some implementations can provide the plurality of segments as linear segments connected in an S-pattern.

In some implementations, a method for providing a wrist mechanism for a surgical instrument includes providing a plurality of link members linked together by cutting portions of a single piece of material, and providing one or more flexures by cutting portions of the single piece of material. At least one of the flexures includes a chain of a connected plurality of segments. Each flexure connects associated adjacent link members and enables rotational movement of the associated link members relative to each other to provide an associated degree of freedom to the end effector. The wrist mechanism provides at least one degree of freedom between the ends of the wrist mechanism.

In some implementations, a wrist mechanism for a surgical instrument includes a plurality of link members linked together, and one or more flexures. Each flexure connects associated adjacent link members and enables rotational movement of the associated link members relative to each other to provide an associated degree of freedom to the end effector. At least one stop member is coupled to one of the link members between associated adjacent link members, where the stop member prevents the rotational movement between the associated link members beyond a predetermined angular range. The stop member is provided on one link member and engages a receiving recess in the opposing side end of the associated link member in response to the link members being rotated by a predetermined amount with respect to each other. The link members, at least one stop member, and flexures are formed from a single piece of material, and the wrist mechanism provides at least one degree of freedom between the ends of the wrist mechanism.

DETAILED DESCRIPTION

The present disclosure relates generally to surgical instruments and, more particularly, to wrist linkages in surgical instruments used to perform surgery, such as robotic surgery. In some implementations, a surgical instrument includes an end effector and a unitary wrist mechanism coupled to the end effector, where the wrist mechanism is formed from a single piece of material and provides at least one degree of freedom to the end effector. The wrist mechanism includes multiple link members linked together and one or more flexures. Each flexure connects associated adjacent link members and enables rotational movement of the associated link members relative to each other to provide an associated degree of freedom to the end effector. For example, the link members can be approximately cylindrical and the wrist mechanism can provide at least two degrees of freedom to the end effector, such as about a pitch axis and a yaw axis. The flexures can be connected between opposing end sides of associated link members, and in some implementations the flexures can include a chain of linear segments connected in an S-pattern.

Features of the wrist mechanism described herein allow a surgical instrument to provide one or more degrees of freedom to an end effector with significantly reduced cost. For example, the wrist mechanism is formed from a single piece of material, thus greatly reducing the cost of assembling separately-made multiple stages in a linkage. The link members of the wrist mechanism do not require as precise or as much tensioning for use with cables or other tendon force transmission control mechanisms, since tension does not hold the link members together. Wear properties of the wrist mechanism material allow a large number of uses of the wrist mechanism before its components reduce in strength or function. Furthermore, the wrist mechanism in some implementations can be low enough in cost to use disposably on some surgical instruments, saving cleaning costs for surgical procedures.

In the disclosure herein, the term "flexible" and "flex" in association with a part, such as a mechanical structure, component, or component assembly, should be broadly construed. In essence, the term means the part can be repeatedly bent and restored to an original shape without harm to the part. Many "rigid" objects have a slight inherent resilient "bendiness" due to material properties, although such objects are not considered "flexible" as the term is used herein. For example, a short, flexible part may serve as, and be modeled as, a single mechanical constraint (joint) that provides one or more DOF's between two links in a kinematic chain, even though the flexible part itself may be a kinematic chain made of several coupled links. The terms "parallel," "perpendicular," "aligned," or particular measurements in degrees or other units as used herein need not be exact and can include typical engineering tolerances.

Figure 1:
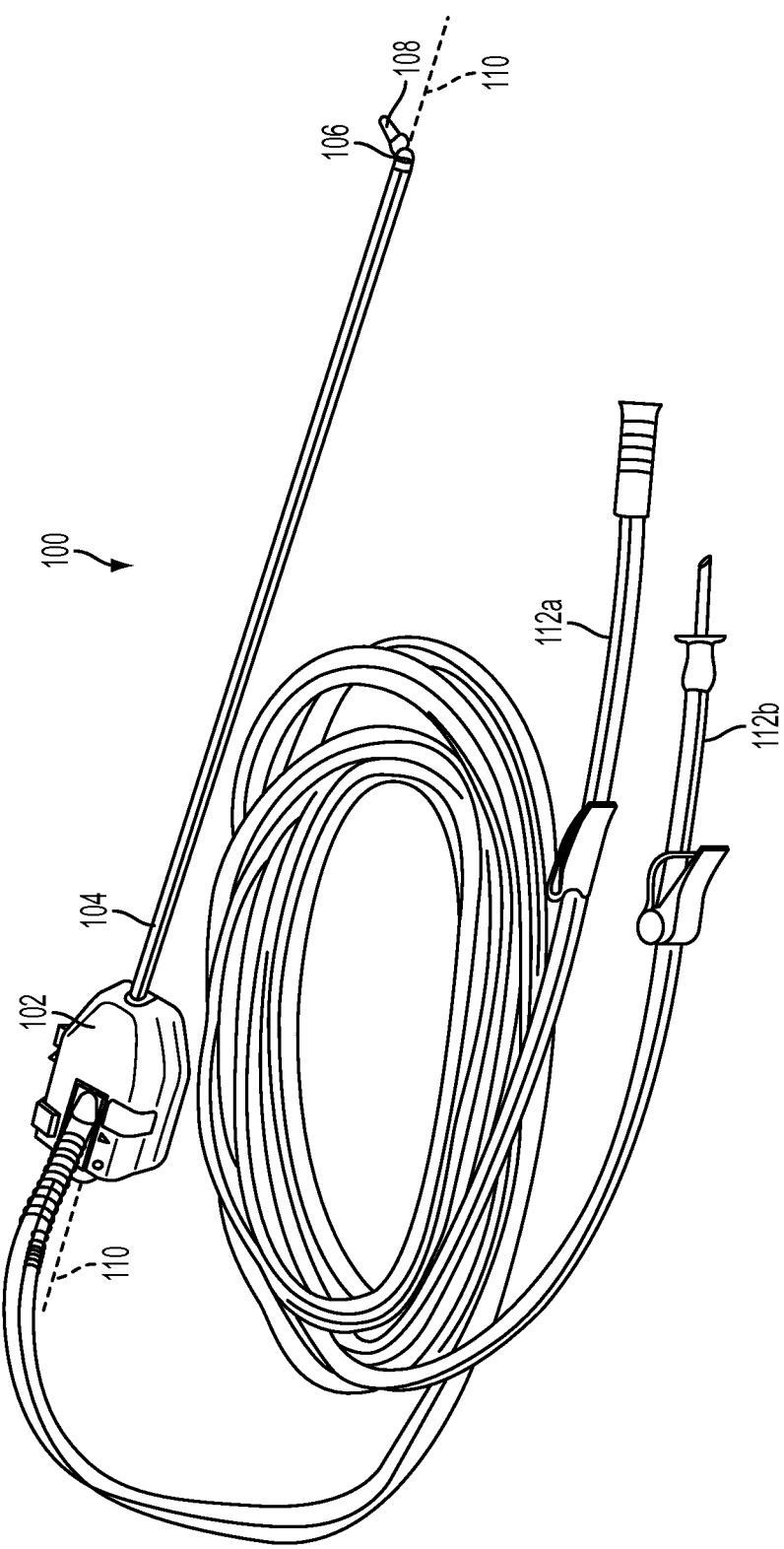
FIG. 1 shows a perspective view of an example implementation of a surgical instrument suitable for some implementations of the wrist mechanisms described herein.

FIG. 1 is a perspective view of an example implementation of a surgical instrument 100 that is suitable for some implementations of the wrist mechanisms described herein. Instrument 100 is an example of a minimally invasive surgical instrument used for surgical procedures on patients. Various other types of surgical instruments, both manually and robotically operated, can alternatively be used with the wrist mechanisms described herein. In the example of FIG. 1, surgical instrument 100 includes a proximal end mechanism 102, an elongate shaft 104, a wrist mechanism 106, and an end effector 108.

Proximal end unit 102 can, in some implementations, be removably connected to a surgical robotic manipulator arm. One example of such a manipulator arm is a da Vinci® surgical system instrument manipulator arm available from Intuitive Surgical, Inc. of Sunnyvale, Calif. Components in proximal end unit 102 can function as force transmission mechanisms to receive teleoperated servo actuation forces from the surgical robotic manipulator and, in turn, redirect the received forces to operate components of instrument 100, such as changing the orientation of wrist 104 and operating other components in proximal end unit 102. In some example implementations, proximal end unit 102 receives multiple separate actuation inputs from its associated robotic manipulator, e.g., where the number of actuation inputs depend on the number of instrument 100 features to be controlled. In other examples, proximal end unit 102 can include one or more motors or other actuators that operate associated instrument 100 features, and such motor (s) rather than an external actuator provide force to operate associated features. Some instrument features can include pitch and yaw control of the wrist mechanism 104 to control the pitch and yaw orientation of the end effector 108. Some implementations can also control other instrument features such as the roll of shaft 104, wrist mechanism 106, and end effector 108, the output of material transported through the shaft 104 and out of end effector 108 (e.g., liquid or other fluids), suction forces provided by end effector 108, and/or any of a multiple of other end effector functions (e.g., opening jaws of a grasper, moving a blade, etc.).

In other implementations, the proximal end unit 102 can be connected to a different type of device enabling control of instrument 100 features, or the unit 102 can be manually operated by an operator. For example, controls provided on the unit 102 (or on a different connected device) can allow an operator to manually control the orientation of the wrist mechanism 106 and end effector 108.

Elongate shaft 104 couples proximal end unit 102 to end effector 108, allowing end effector 108 to be inserted through a patient's body wall to reach a surgical site while proximal end unit 102 remains outside the patient. For purposes of this description, a longitudinal axis 110 is defined along the centerline of shaft 104 for instrument 100. In an example implementation, the outer diameter of shaft 104 can be about 8 mm, although this dimension can be varied for other implementations. Shaft 104 can be substantially rigid, or flexible in other implementations. According to some implementations, shaft 104 may include a cavity, such as a tube, that provides material transfer along the shaft. For example, material may be transferred between a distal end of shaft 104 and a proximal end of shaft 104, or points near the proximal end and near the distal end of shaft 104.

Wrist mechanism 106 is coupled between the distal end of shaft 104 and end effector 108. Features of wrist mechanism 106 are described in greater detail below. In the depicted implementation, wrist mechanism 106 allows end effector 108 to change orientation with two degrees of freedom (DOFs), arbitrarily termed pitch and yaw, with reference to longitudinal axis 110. In some implementations, wrist mechanism 106 can enable only a single DOF (e.g., pitch or yaw), or in other implementations, wrist mechanism 106 can enable more than two DOFs, e.g., so that compound curves can be controlled.

End effector 108 is positioned at the distal end of the instrument 100. The end effector 108 can be used to provide any of a variety of functions. In some examples shown herein, the end effector is configured to provide an irrigation function and/or a suction function at a surgical site. In some example implementations, an enclosed channel (such as a tube) forming a lumen can extend from end effector 108, through wrist 106 and shaft 104, to proximal end unit 102, where the end unit 102 can control whether a suction or irrigation function is enabled in instrument 100. In other implementations, the end effector 108 can be or include other mechanisms or pieces, such as a scalpel or cutting blade, scissors, forceps, retractor, dilator, clamp, cauterizing tool, needle, needle driver, stapler, drill, probe, scope, light source, guide, measurement device, vessel sealer, laparoscopic tool, or other tip, mechanism or device.

Some implementations can include connection features such as example flexible tubes 112a and 112b connected to the proximal end unit 102. For example, flexible tube 112a can couple a surgical irrigation fluid (liquid or gas) source (not shown) to surgical instrument 100 so that irrigation fluid can be routed from a source through feature 112a, through proximal end unit 102, through a linear inside tube (not shown) extending along the length of shaft 104, and through wrist mechanism 106 to exit via end effector 108. Similarly, flexible tube 112b can couple a surgical suction source (not shown) to instrument 100 so that material from a surgical site can be drawn into end effector 108 and through wrist mechanism 106, through a tube in shaft 104, through proximal end mechanism 102, and through flexible tube 112b, to the source. Other types of connection features can be provided in other implementations.

Other implementations can use other types of surgical instruments that include a wrist mechanism including one or more features described herein. For example, components of different dimensions can be used, such as a shaft 104 of different width and/or length, or having a curved shape rather than the linear shape shown. A flexible shaft instead of shaft 104 can be provided in some implementations to allow the instrument to conform to a shape or route of a passage (e.g., cannula sleeve) through which the instrument is to be moved.

Figure 2:
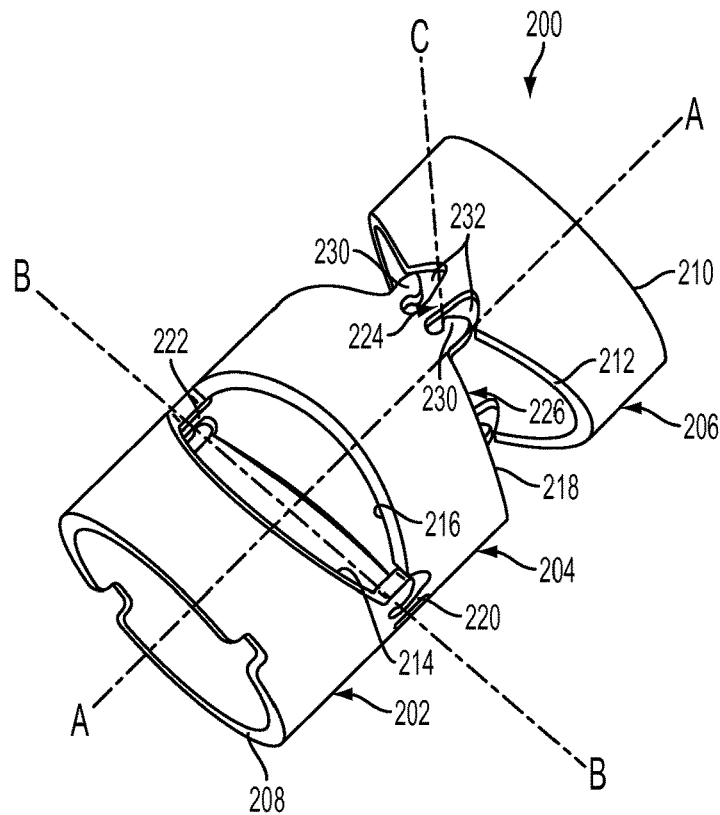
FIG. 2 shows one example implementation of a wrist mechanism including one or more features described herein.

FIG. 2 is a perspective view of one example implementation of a wrist mechanism 200 including one or more features described herein. For example, wrist mechanism 200 can be used in surgical instrument 100 or similar instrument as wrist mechanism 106.

The example wrist mechanism 200 includes multiple link members that are linked together in a linkage. In this example, the link members are serially linked together. The wrist mechanism 200 includes a link member 202 coupled to a link member 204, which is in turn coupled to a link member 206.

The link members can be provided in any of a variety of different shapes or configurations. For example, the link members 202-206 can be annular and cylindrical or approximately cylindrical in shape as shown, having curved sidewalls and end sides (or faces) on opposite ends of each cylinder. In a neutral state of the linkage as shown in FIG. 2, the link members of the linkage are centered or approximately centered along a longitudinal axis A that is parallel to the sidewalls, which can be longitudinal axis 110 in an example of FIG. 1. The end sides of each link member can be perpendicular or approximately perpendicular to the axis A on some cylinder ends, such as end sides 208 and 210. On other cylinder ends that are adjacent to other link members, the end portions can be angled or tapered with respect to the perpendicular direction to the axis A to allow rotational motion between the adjacent link members. For example, the end side 212 is adjacent to connected link member 204 and can be tapered in directions away from the connected link member 204 such that the length of the cylindrical link member 206 (along axis A) is lower at the furthest points from the flexures 224 and 226 on the end side 212. The middle, second link member 204 can include two such tapered end portions 216 and 218 since it has two adjacent link members. Other implementations can provide non-angled end portions or sides angled in other directions.

In other implementations, the link members can be formed in other shapes. For example, planar surfaces, rectilinear shapes, or other shapes can be used, and/or different shapes or forms for inner surfaces and/or outer surfaces of the link members. Some implementations can use partial cylinders in which gaps or portions of the cylinders may be absent. Other implementations can use other forms of members, extensions, or links.

In some example implementations of surgical instruments that include wrist mechanism 200, the link member 202 can be a distal link member coupled to an end effector on a side opposite to the second link member 204, and the link member 206 can be a proximal link member that is coupled to a proximal portion of the instrument on a side opposite to the second link member 204. For example, in the example surgical instrument 100 of FIG. 1, the link member 206 can be coupled to the shaft 104 on the side 210 opposite to the second link member 204, and the third link member 202 can be coupled to the end effector 108 on the side 208 opposite to the second link member 204.

The link members of wrist mechanism 200 are coupled to each other by one or more flexures. Each flexure (or flexible hinge) is flexible member that couples two other relatively rigid members. In the example of FIG. 2, each link member can be a relatively rigid member that is coupled to an adjacent link member by two flexures, although a different amount of flexures can be used in other implementations. Each flexure is a piece of material that flexes to allow pivoting or rotation of attached members about an axis of rotation extending through a portion of the flexure. For example, in some implementations the axis of rotation extends perpendicularly or approximately perpendicularly to the lengthwise axis of a flexure and approximately through a center of the flexure, such as axes of rotation B and C. In other implementations the axis of rotation extends through a different portion of the flexure that has been configured to flex based on forces applied to the wrist mechanism. In some examples, a thinnest portion of the flexure may allow the easiest flexing motion and the axis of rotation may be centered thereon. In some implementations, the flexure allows flexing in one degree of freedom (such as one axis of rotation) but is substantially rigid in other degrees of freedom (such as axes of rotation in other directions), thus preventing or reducing flexure in those other degrees of freedom. For example, the flexure can be made thin in a dimension allowing the desired flexure, and thicker or wider in dimensions in which flexure and rotation are not desired.

In the implementation shown in FIG. 2, a flexure 220 is coupled between first link member 202 and second link member 204 at one location on the curved sidewall of the cylindrical link members. For example, flexure 220 is coupled between the end side 214 of link member 202 and the end side 216 of the link member 204. Flexure 222 is coupled between the end sides 214 and 216 about 180 degrees away from the flexure 220 along the sidewalls of link members 202 and 204. Similarly, flexures 224 and 226 are coupled about 180 degrees apart between the end side 218 of link member 204 and the end side 212 of the link member 206. In the implementation shown, flexures 224 and 226 can be positioned 90 degrees (or approximately so positioned) around axis A relative to the flexures 220 and 222.

The flexures of wrist mechanism 200 flex to act as joints between adjacent link members, thus providing particular degrees of freedom between the link members of the wrist mechanism, e.g., to an attached object such as an end effector. For example, two degrees of freedom are provided between the ends 208 and 210 of the wrist mechanism. One rotational degree of freedom is provided about axis B that extends through the flexures 220 and 222, where axis B is nonparallel to, e.g., perpendicular or approximately perpendicular to, the longitudinal axis A. This degree of freedom allows the link members 202 and 204 to rotate with respect to each other about axis B, and allows any object attached to either of these link members to similarly rotate. Another degree of freedom is provided about axis C that extends through the flexures 224 and 226, where axis C is nonparallel to, e.g., perpendicular or approximately perpendicular to, the longitudinal axis A. This degree of freedom allows the link members 204 and 206 to rotate with respect to each other about axis C, and allows any object attached to either of these link members to similarly rotate. In this example, axis B is nonparallel to axis C, e.g., perpendicular or approximately perpendicular to axis C, thus providing two transverse degrees of freedom about axes B and C. Other implementations can provide degrees of freedom about axes that are positioned and/or oriented differently relative to each other.

In some implementations, flexures 220-226 can also provide an inherent return spring force to the associated link members connected by the flexures (e.g., elastic deformation). For example, this spring force can bias the rotational positions of the link members about axes B and C to the neutral position shown in FIG. 2. The spring force can be overcome by forces transmitted to the wrist mechanism by a transmission system, as described below. In other implementations, one or more materials can be used for one or more flexures 220-226 that do not provide return spring force (e.g., plastic deformation).

Wrist mechanism 200 can also include stop members associated with each flexure to enable a stop or limit to flex motion, guide the rotation of the link members, and/or reduce flex in undesired directions. For example, stop members 230 can be positioned on opposite sides of flexure 224 extending out from the end side 218 of link member 204 toward the adjacent link member 206. The stop members 230 are aligned with associated recesses 232 in the end side 212 of link member 206. When the link members 204 and 206 are made to rotate about axis C relative to each other, one of the stop members 230 will engage its associated recess 232. In some implementations, this engagement can include engaged surfaces of the stop members 230 and associated recesses 232 contacting and sliding against each other, to guide the rotation of the members. In other implementations, the engagement allows the stop member 230 surface facing the associated recess 232 to be positioned close to but does not contact the surface of the associated recess (except for the leading surface of member 230 when reaching the limit to motion in that degree of freedom). The engagement can prevent or reduce undesired torsional flex of the flexures 224 and 226 about axis A, which may occur in some implementations of the flexures. Furthermore, the stop member can act as a stop to limit the rotation of the link members about axis C to a particular desired angular range of rotation by moving against the side of the flexure 224 and/or the associated recess 232. Such features are similar as those described below with respect to FIGS. 7A and 7B. The stop member 230 and associated recess 232 on the opposite side of the flexures 224 and 226 similarly limit motion in the opposite rotational direction about axis C. Each flexure of the wrist mechanism can similarly include stop members and associated recesses.

The linkage of link members 202-206 collectively forms an approximate linear cylindrical shaft when the wrist mechanism is in a neutral state, e.g., when the flexures of the mechanism are in their neutral, unflexed states as shown in FIG. 2. For example, the sidewalls and central longitudinal axes of the cylindrical link members are parallel or approximately parallel in the wrist mechanism's neutral state. If any of the link members are rotated about axis B and/or axis C, then the link members are rotated with respect to each other and their longitudinal axes and sidewalls may no longer be approximately parallel to each other.

The wrist mechanism 200 is a unitary mechanism in which the link members and flexures of the mechanism have been formed from a single piece of material. For example, the flexures 220, 222, 224, and 226 can be formed by cutting material from the same material piece from which the link members 202, 204, and 206 are formed and thus are already attached to their respective link members once the material is cut. A variety of cutting techniques can be used to form the components of the wrist mechanism from a single piece of material, such as laser cutting. Thus, no separate assembly of the components of wrist mechanism 200 need be made; e.g., no welding, gluing, or fastening mechanism (e.g., pin or joint mechanism) need be used to join the link members and flexures. This can lead to significant reduction of assembly time and cost for the wrist mechanism 200.

Wrist mechanism 200 can be made of any of a variety of suitable materials. For example, chromium cobalt is one example readily-available and low-cost material which can be used. Such a material is flexible enough to allow the flexures of the mechanism to readily flex and allow the desired motion. The material is also stiff enough to provide zero or very small axial (torsional) compliance of the mechanism about axis A. This material is easy to laser-cut and has high durability and endurance, so that the flexures of the mechanism can withstand large numbers of flexes before their structure is compromised. Other examples of materials can include other biocompatible (e.g., non-toxic to patient tissue) metals and polymers, including composites.

Additional link members can be provided in the linkage of wrist mechanism 200 in other implementations. Such additional link members can provide additional degrees of freedom and a greater range of motion for the end effector coupled to one end of the linkage. For example, additional link members can be coupled between the end link members 202 and 206 to form a longer chain of link members, and can be formed and coupled similarly as the link member 204 to adjacent link members on both sides. Such additional link members can have their coupled flexures positioned to provide axes of rotation similar to axes B and C at desired orientations.

Figure 3:
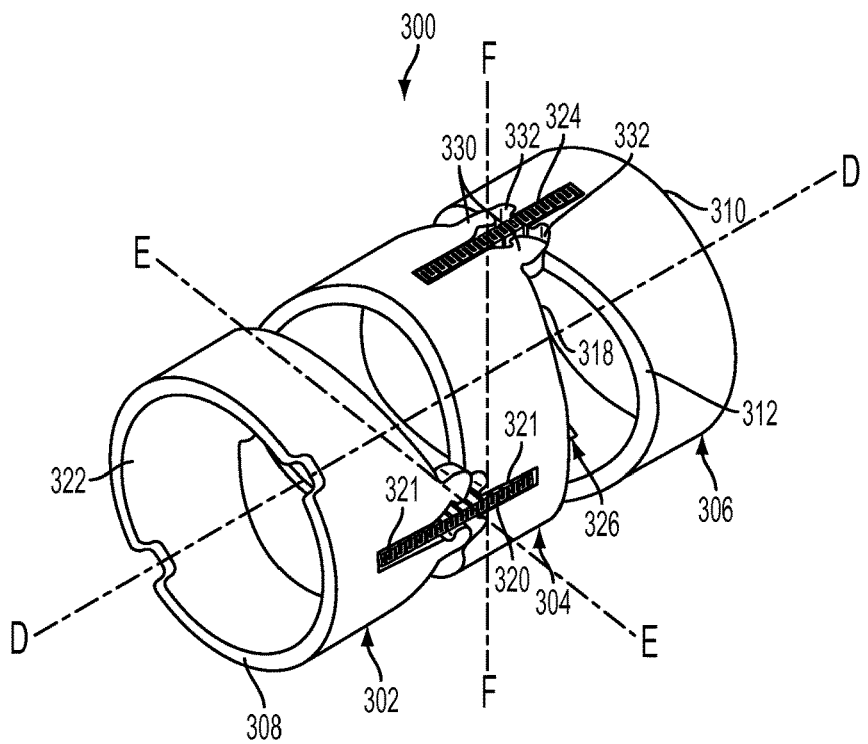
FIG. 3 shows another example implementation of a wrist mechanism including one or more features described herein.

FIG. 3 is a perspective view of another example implementation of a wrist mechanism 300 including one or more features described herein. Wrist mechanism 300 includes some features that are similar to wrist mechanism 200 described above, including a linkage including linked link members 302, 304, and 306, which can be serially linked together in the shown implementation.

Link member 302 is provided at one end of the linkage and can be, for example, a distal link member coupled to an end effector. Link member 306 is provided at the other end of the linkage and can be, for example, a proximal link member that can be coupled to a shaft or other portion of a surgical instrument. Link member 304 is coupled between the link members 302 and 306. In a neutral, unflexed state of the linkage as shown, a longitudinal axis D extends through the lengthwise approximate center of the linkage, which can be longitudinal axis 110 in an example of FIG. 1.

The link members of wrist mechanism 300 can be provided in any of a variety of different shapes or configurations similarly as the mechanism described above for FIG. 2. For example, the link members 302-306 can be annular and cylindrical or approximately cylindrical in shape as shown, having curved sidewalls and end sides on opposite sides of each cylinder. The end sides of each link member can be perpendicular or approximately perpendicular to the axis D on some cylinder ends, such as end sides 308 and 310. On other cylinder ends adjacent to other link members, the end sides can be angled or tapered with respect to the perpendicular direction to the axis D to allow rotational motion between the adjacent link members, similarly as described above for FIG. 2. The linkage of link members 202-206 collectively forms an approximate linear cylindrical shaft when the wrist mechanism is in a neutral state, e.g., when the flexures of the mechanism are in their neutral, unflexed states as shown in FIG. 3. The link members can be formed in other shapes in other implementations.

Each link member is coupled to adjacent link member(s) by one or more flexures, e.g., two flexures in this example. For example, flexure 320 connects relatively rigid link members 302 and 304 at one location along the curved sidewalls of the link members, and a similar flexure 322 (partially shown) connects the link members 302 and 304 at a location of the sidewalls opposite or approximately opposite to the flexure 320, e.g., on the opposite side of longitudinal axis D to the flexure 320, such as about 180 degrees from the flexure 320 around the axis D and sidewall of the link member. Each flexure can be coupled to an associated link member at a point within a recess 321 further within the material of each link member from the end side surface, as shown, and which is described below with respect to FIGS. 7A and 7B. Similarly, flexure 324 connects link members 304 and 306 at one location along the curved sidewalls of the link members, and a similar flexure 326 (partially shown) connects the link members 304 and 306 at a location along the sidewalls on the opposite or approximately opposite side of axis D to the flexure 324. In this example, flexures 324 and 326 are positioned 90 degrees (or approximately so positioned) rotationally around axis D relative to the flexures 320 and 322.

Each flexure is a single piece of material that has been formed to flex and act as a joint between adjacent link members that are rigid relative to the flexure. In the implementation shown in FIG. 3, the flexures 320-326 each include an S-shaped structure that can allow flexing by a stiffer material than the material of the implementation of FIG. 2. Such a structure is described in greater detail below with respect to FIGS. 7A-7B. The flexing motion of the flexures allows pivoting or rotation of attached members about an axis of rotation extending through a portion of the flexure. For example, in some implementations the axis of rotation extends perpendicularly or approximately perpendicularly to the lengthwise axis of a flexure and approximately through a center of the flexure, such as axes of rotation E and F. In other implementations the axis of rotation can extend through a different portion of the flexure that has been configured to flex more easily than other portions of the flexure. In some implementations, the flexure allows flexing in one degree of freedom (such as one axis of rotation) but is substantially rigid in other degrees of freedom (such as axes of rotation in other directions), thus preventing or reducing flexure in those other degrees of freedom.

The flexures of wrist mechanism 300 flex to provide particular degrees of freedom to an object attached to the mechanism 300, such as an end effector. One rotational degree of freedom is provided about axis E that extends through the flexures 320 and 322, where axis E is nonparallel to, e.g., perpendicular or approximately perpendicular to, the longitudinal axis D. This degree of freedom allows the link members 302 and 304 to rotate with respect to each other about axis E, and allows any object attached to either of these link members to similarly rotate. Another degree of freedom is provided about axis F that extends through the flexures 324 and 326, where axis F is nonparallel to, e.g., perpendicular or approximately perpendicular to, the longitudinal axis D. This degree of freedom allows the link members 304 and 306 to rotate with respect to each other about axis F, and allows any object attached to either of these link members to similarly rotate. In this example, axis E is nonparallel to the axis F, e.g., perpendicular or approximately perpendicular to axis F, thus providing two transverse degrees of freedom about axes E and F. Other implementations can provide degrees of freedom about axes that are positioned and/or oriented differently relative to each other.

Flexures 320-326 can also provide an inherent spring force to the associated link members connected by the flexures. For example, this spring force can bias the rotational positions of the link members about axes E and F to the neutral position shown in FIG. 3. The spring force can be overcome by forces transmitted to the wrist mechanism by a transmission system, as described below. Other implementations may not provide such a spring force similarly as described above for FIG. 2.

Wrist mechanism 300 can also include stop members associated with each flexure. For example, stop members 330 can be positioned on opposite sides of flexure 324 and extend out from the end side 318 of link member 304 toward the adjacent link member 306. The stop members 330 can engage with recesses 332 in the adjacent link member 306. Each flexure of the wrist mechanism 300 can similarly include stop members and associated recesses. Such stop members and recesses are described in greater detail below with respect to FIGS. 7A and 7B.

The wrist mechanism 300 is a unitary mechanism in which the link members of the mechanism have been formed from a single piece of material. For example, the flexures 320, 322, 324, and 326 can be formed by cutting material from the same material piece from which the link members 302, 304, and 306 are formed and thus are already attached to their respective link members once the material is cut. A variety of cutting techniques can be used to form the components of the wrist mechanism from a single piece of material. For example, laser cutting can be used to provide precise cuts in the material of the mechanism. Thus, no separate assembly of the components of wrist mechanism 300 need be made. This can lead to significant reduction of assembly time and cost for the wrist mechanism 300.

Wrist mechanism 300 can be made of any of a variety of suitable materials. For example, Nitinol™ is one example readily-available and low-cost material which can be used. Such a material is a "super-elastic" material that can allow the flexures of the mechanism to readily flex and allow the desired motion, while providing sufficient stiffness to provide very small axial compliance of the mechanism about axis D. This material is easy to laser-cut and has high durability and endurance, so that the flexures of the mechanism can withstand large numbers of flexes before their structure is compromised. Other examples of materials can include tempered stainless steel, other carbon steels, chromium cobalt, or other material that has resilience and is not toxic for use in surgical procedures.

Additional link members can be provided in the linkage of wrist mechanism 300 in other implementations, such as in a chain configuration as similarly described above for wrist mechanism 200 of FIG. 2. Such additional link members can provide additional degrees of freedom and/or a greater range of motion for the end effector coupled to an end of the linkage.

Figure 4:
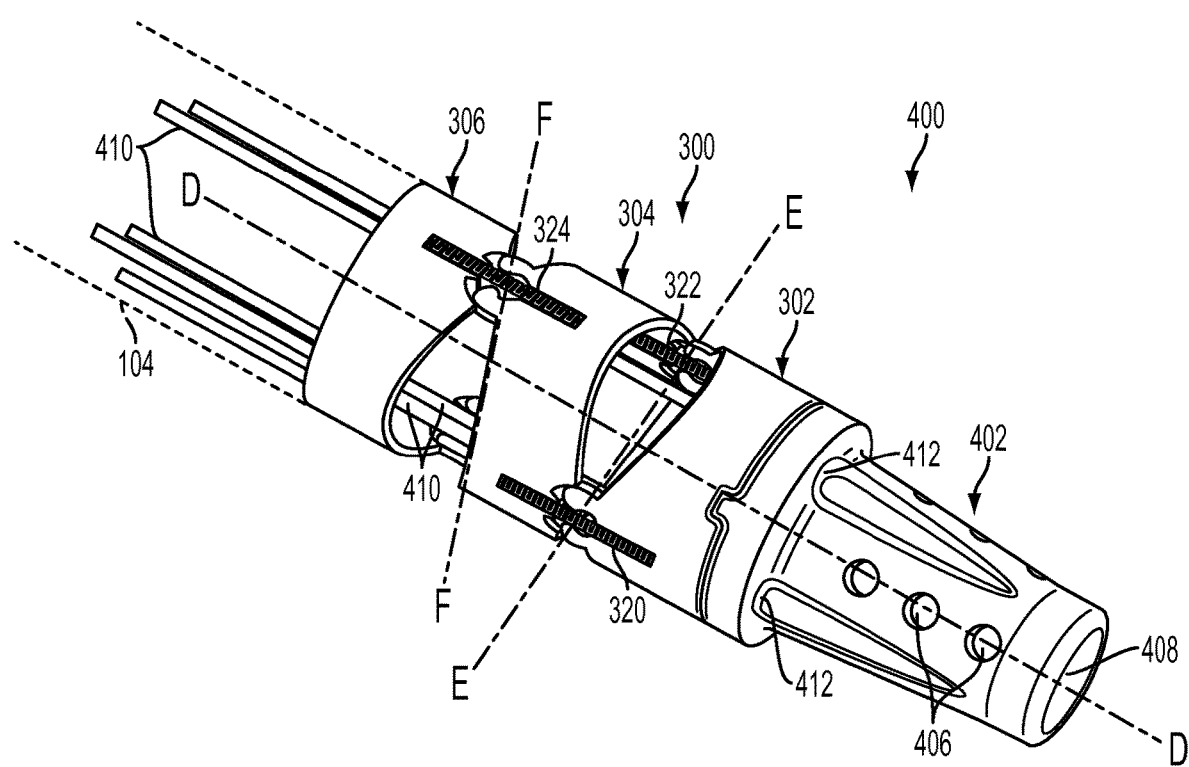
FIG. 4 shows a perspective view of an example portion of a surgical instrument, including the wrist mechanism of FIG. 3 and an end effector.

FIG. 4 is a perspective view of an example portion 400 of a surgical instrument, including a wrist mechanism 300 similar to the mechanism shown in FIG. 3 and an end effector 402. For example, portion 400 of a surgical instrument can be provided at the distal end of an instrument such as surgical instrument 100 of FIG. 1.

An end effector 402 can be coupled to one end of the wrist mechanism 300. For example, link member 302 can be coupled to the end effector 402 and link member 306 can be coupled to the shaft 104. In this example, end effector 402 is a tool used for irrigation and/or suction at the surgical site. For example, fluid that is input to the instrument via flexible tube 112a can be guided down the middle of the instrument 100 in a central tube (see FIG. 6) or other lumen extending along the approximate center of shaft 104 and the hollow central portion of wrist mechanism 300, where the central tube is connected to the end effector 402. The central tube can be flexible in at least the portion extending through the wrist mechanism 300 to accommodate movement of the wrist mechanism in one or more degrees of freedom. The fluid flows through and exits the end effector 402, such as through one or more side holes 406 of the end effector, and/or through a central hole 408 at the tip of the end effector. Suction can similarly be used in the reverse direction, where air suction can be used to draw fluids or other objects at the surgical site through the holes 406 and/or 408, up the central tube through shaft 104, and through the flexible tube 112b. Other types of end effectors can be coupled to the wrist mechanism 300 in other implementations, as described above. In other implementations, one or more different or additional elongated members, extensions, or components can be routed through the central hollow space of shaft 104, wrist mechanism 300, and/or end effector 402, such as one or more fiber optic cables, electrical cables, mechanical push rods, micro-rivets, self-forming staples, etc.

The wrist mechanism 300 can be controlled to move in two degrees of freedom about axes E and F, e.g., each degree of freedom providing angular motion within a plane oriented in three-dimensional space. Any suitable form of force transmission mechanism can be used to allow a user or controller device to initiate and control movement of the wrist mechanism 300 about these axes. In the example of FIG. 4, tendons are used in a force transmission mechanism. For example, the tendons can be cables 410 that are routed from a proximal side of the surgical instrument, through the shaft 104, and through the center region of the wrist mechanism 300, to be connected to the end effector 402, e.g., at termination holes 412 of the end effector. In the example of FIG. 4, four cables 410 are shown, where each cable 410 is routed along the interior of the cylindrical link members near to one of the flexures 320-326, and each cable is spaced apart from the two other cables by about 90 degrees around longitudinal axis D. Two of the cables 410 are used to control motion in one degree of freedom of the wrist mechanism 300 (e.g., about axis E, or arbitrarily named a pitch degree of freedom), and the other two cables 410 are used to control motion in the other degree of freedom (e.g., about axis F, or yaw degree of freedom). This operation is described in greater detail below with respect to FIGS. 5A and 5B. Additional degrees of freedom can be supported and controlled in some implementations. For example, a roll motion of the shaft 104, wrist mechanism 300, and end effector 402 can be implemented about the axis D, which can be similarly controlled at the proximal side of the surgical instrument 104.

The cables 410 can be controlled by a control mechanism provided in and/or coupled to a surgical instrument that includes the wrist mechanism 300, such as surgical instrument 100. In some implementations, the control mechanism can include a drive system providing actuators such as servomotors which can pull and/or push the cables 410 appropriately to provide desired movement in the degrees of freedom about axes E and F. For example, two of the cables 410 that are opposing each other on opposite sides of the central axis D can be two ends of a single cable that is engaged by a pulley or spindle driven rotationally by an actuator. The other two cables 410 can similarly be ends of a single cable controlled independently by a different pulley and actuator. Alternatively, cables 410 can be separate cables connected to a single or different pulleys and independently controllable. For example, such pulleys and/or actuators can be provided in the proximal end unit 102 shown in FIG. 1, or in a different connected mechanism. In some embodiments, each pulley can be driven by a servomotor controlled by a robotic surgery system. Some example implementations of such a system are disclosed in U.S. Patent Pub. No. 2013/0046318, which is incorporated herein by reference in its entirety. In other implementations, other mechanisms can be used to move the cables 410, such as a gimbal mechanism as disclosed in U.S. Pat. No. 6,817,974, which is incorporated herein by reference in its entirety.

In some implementations, the cables can be pretensioned for connection to the end effector through the wrist mechanism. This can allow a fine degree of control over the motion of the link members in the rotational degrees of freedom about axes D and E and can compensate for cable stretch that can lead to less precise control. However, the amount of pretension required can be considerably less than in prior linkages in which cable tension held the link members of a wrist mechanism together, unlike implementations described herein.

Other types of tendons, transmission mechanisms, and/or actuators can be used in other implementations. For example, force transmission elements can be cables, wire, filaments, or rods, and/or compression elements, such as, for example, rigid rods, shafts or tubes that can be used in place of cables in sections of the transmission system to transmit forces to the wrist mechanism.

Figure 5A:
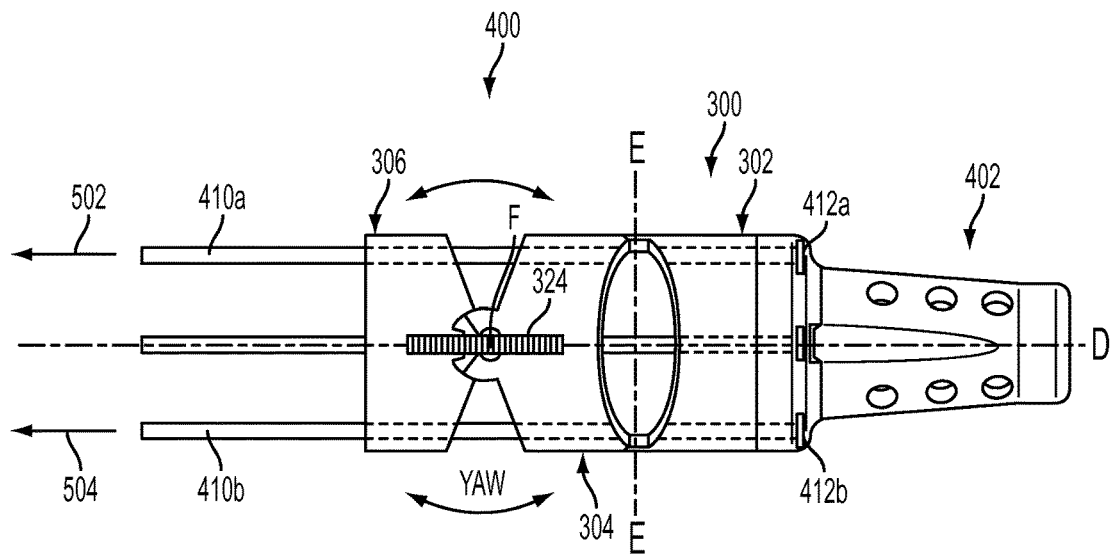
FIGS. 5A, 5B, and 5C show top, side, and front views, respectively, of the portion of the surgical instrument shown in FIG. 4.
Figure 5B:
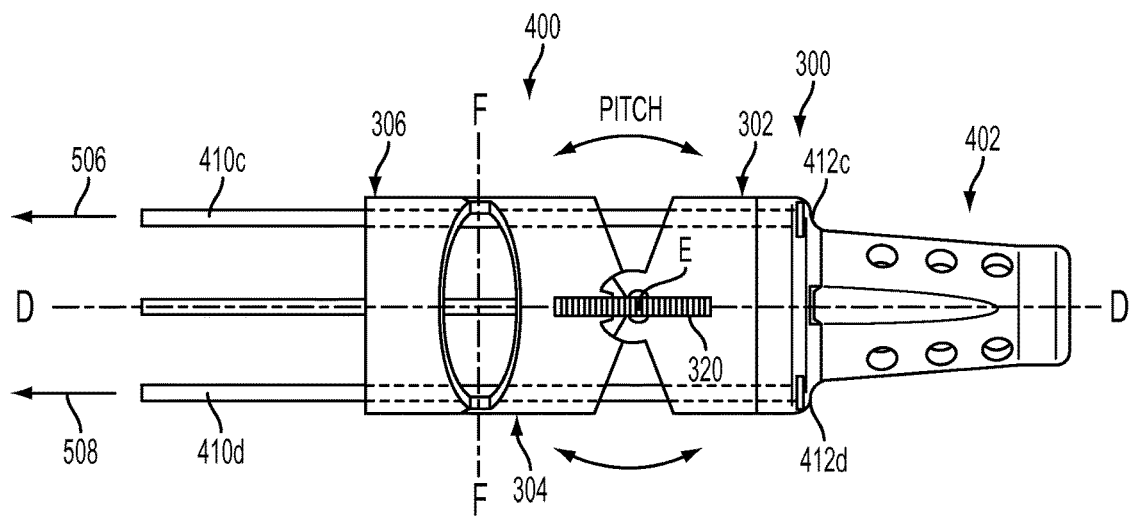

FIGS. 5A and 5B are top and side views, respectively, of the portion 400 of the surgical instrument shown in FIG. 4. In FIG. 5A, a yaw degree of freedom including rotational motion of the wrist mechanism 300 about axis F is shown. This degree of freedom is allowed by flexures 324 and 326 on opposite sides of axis D and connecting link members 306 and 304, permitting the end effector 402 to be rotated about axis F.

The motion shown in FIG. 5A can be caused and controlled by the movement of cables 410. In this example, cables 410a and 410b (which can be the two ends of a single cable as described above, or two independent cables) can be moved to cause the end effector 402, link member 302, and link member 304 to flex about axis F with respect to link member 306 and the portion of the surgical instrument connected to link member 306. For example, the end of cable 410a can be connected to the end effector at termination hole 412a and that cable can be pulled toward the proximal end of the surgical instrument as indicated by arrow 502. This pulling force causes flexures 324 and 322 to flex and causes the end effector and link members 302 and 304 to rotate about axis F in the counterclockwise direction in the view of FIG. 5A. In implementations in which cable 410b is part of the same cable as cable 410a, the motion of 410a is accompanied by motion of cable 410b in the opposite direction toward the end effector 402. This can, in some implementations, provide a pushing force on the end effector at the connection point of the cable 410b with the end effector, e.g., at termination hole 412b, and further contributing to the counterclockwise motion about axis F. In some implementations, the cable 410b can be a separate cable that can be pushed to accompany with the pulling motion of cable 410a.

Similarly, cable 410b can be connected to the end effector at termination hole 412b and that cable can be pulled toward the proximal end of the surgical instrument as indicated by arrow 504. This pulling force causes flexures 324 and 322 to flex and causes the end effector and link members 302 and 304 to rotate about axis F in the clockwise direction in the view of FIG. 5A. The motion of cable 410b can be accompanied by motion of cable 410a in the opposite direction toward the end effector 402 which in some implementations can provide a pushing force on the end effector and contribute to the clockwise motion about axis F.

In FIG. 5B, a pitch degree of freedom including rotational motion of the wrist mechanism 300 about axis E is shown. This degree of freedom is allowed by flexures 320 and 322 on opposite sides of axis D which connect link members 302 and 304.

The motion shown in FIG. 5B is caused and controlled by the movement of cables 410c and 410d, which can be ends of a single cable as described above, or two independent cables, and can be moved to cause the end effector 402 and link member 302 to flex about axis E with respect to link members 304 and 306 and the portion of the surgical instrument connected to link member 306. For example, the end of cable 410c can be connected to the end effector at termination hole 412c and that cable can be pulled toward the proximal end of the surgical instrument as indicated by arrow 506. This pulling force causes flexures 320 and 322 to flex and causes the end effector and link member 302 to rotate about axis E in the counterclockwise direction in the view of FIG. 5B. The motion of 410c can be accompanied by motion of cable 410d in the opposite direction toward the end effector 402 which can further contribute to the counterclockwise motion about axis E.

Cable 410d can be connected to the end effector at termination hole 412d and that cable can be pulled toward the proximal end of the surgical instrument as indicated by arrow 508. This pulling force causes flexures 320 and 322 to flex and causes the end effector and link member 302 to rotate about axis E in the clockwise direction in the view of FIG. 5B. The motion of cable 410d can be correspondingly accompanied by motion of cable 410c in the opposite direction toward the end effector 402.

Figure 5C:
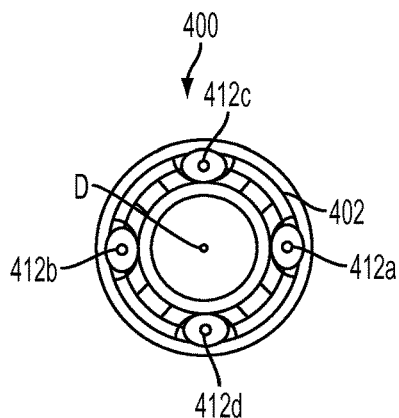

FIG. 5C is a front elevational view of the portion 400 of the surgical instrument shown in FIG. 4. In the described implementation, the termination holes 412a-412d can be located in the end effector 402 around axis D and can receive the ends of cables 410a-410d, respectively. For example, the cables 410a-410d can be swaged to attach to the termination holes 412a-412d, or otherwise attached. In some implementations, the ends of the cables can be laser welded (or welded using other techniques) to a portion of the wrist mechanism 106 or end effector 108. In one example, the cables need not be terminated at the termination holes 412a-412d. For example, cables can be attached to links, where a cable can be actuated to move the link to which it is attached. In some examples, apertures can be cut in the wrist mechanism and the cables can be routed into the apertures and/or back out.

In some implementations of the portion 400, the cables 410a-410d are routed through the wrist mechanism 300 without additional guides or other structures. Other implementations can route cables 410a-410d in other ways through the wrist mechanism 300. For example, a sleeve or separation channel can be integrated for each cable as part of each link member 302, 304, and 306 to guide the cables. Such sleeves can be provided on the inside walls of the link members. For example, sleeves can be aligned or approximately aligned parallel to axis D with the termination holes 412a-412d, and can be enclosed or partially open, allowing the cables to move along their longitudinal axes within the sleeves. In some implementations, such sleeves can continuously run the length of the link members parallel to axis D, or can extend for only a portion of the length of each link member. For example, multiple sleeves of less length than the link members can be provided for each cable, e.g., one or more sleeve sections provided in the link members 302, 304, and 306. The sleeves can be included as part of the unitary material piece of the wrist mechanism 300. In other implementations, the cables 410a-410d can be guided by separate tubes such as nanotubes that have been attached to the inside of the cylindrical members, e.g., aligned with the termination holes 412a-412d. In another example, multilumen hypotubes can be used to route multiple cables. In some implementations, cable-guiding sleeves can be positioned on the outside surface of the sidewalls of the link members, e.g. integrated with the unitary piece of material or separately attached.

Figure 6A:
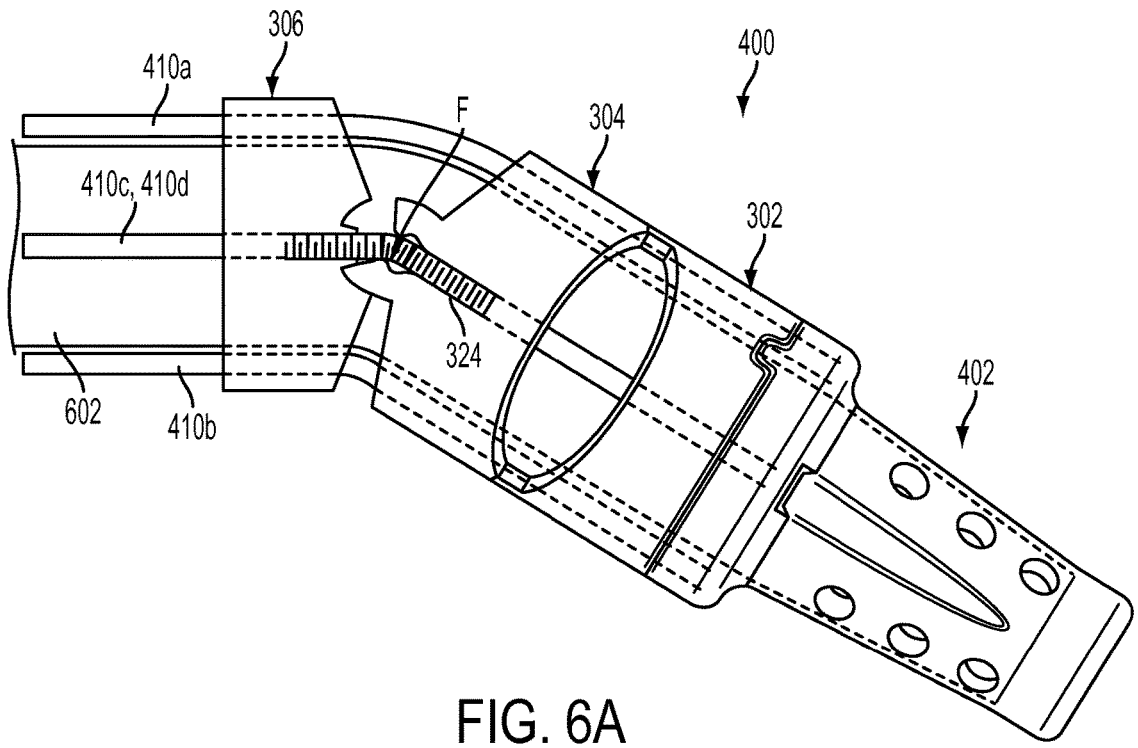
FIGS. 6A and 6B show top and side views, respectively, of the portion of the surgical instrument shown in FIG. 4 in rotated positions.
Figure 6B:
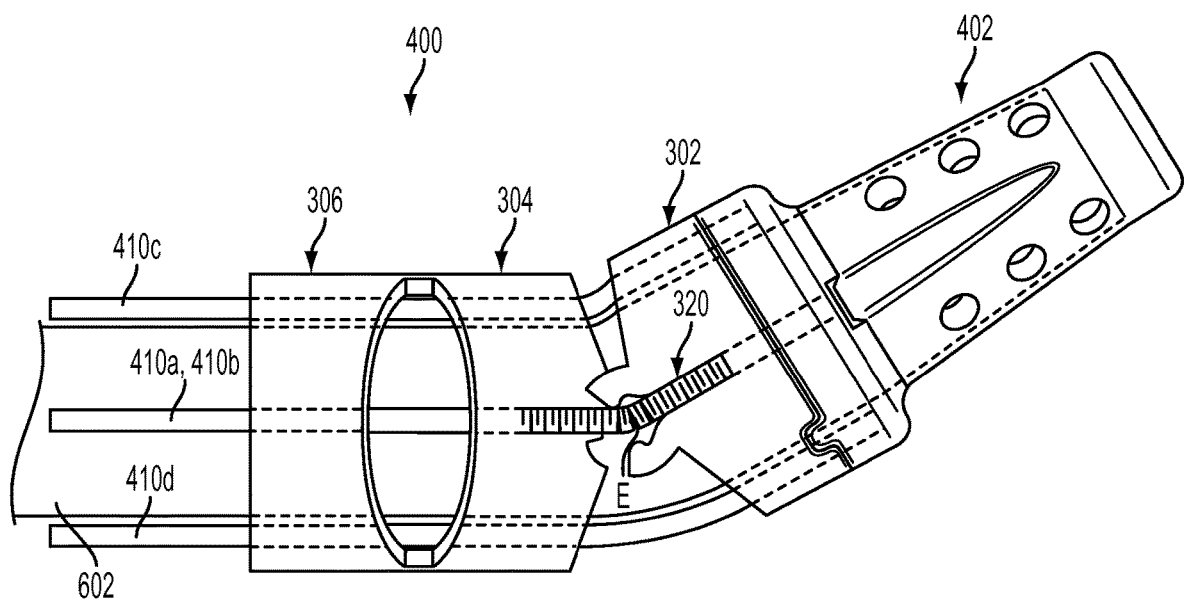

FIGS. 6A and 6B are side and top views, respectively, of the portion 400 of the surgical instrument shown in FIG. 4, where the link members have been rotated. FIG. 6A shows the portion 400 after the link members 304 and 302 and end effector 402 have been rotated in the yaw direction about axis F as indicated in FIG. 5A. Flexure 324 has flexed to accommodate the rotated position of the linkage. In addition, cables 410a-410d have bent with the linkage. In the implementation shown, the cables 410a-410d remain positioned close to the interior sidewalls of the link members through the bend in the linkage. In some examples, this cable positioning can be caused by a central tube 602 running down the interior of the linkage, similarly as the central tube described above with respect to FIGS. 1 and 4, which keeps the cables separated and positioned as shown. Alternatively, the cable positioning can be caused by interior guides or tubes for the cables as described above. In other implementations, the cables can be directly connected to the end effector 402 without being guided or spaced by interior objects or structures, and so may run straight through the interior space of the wrist mechanism 300 or can be curved around and against linkage bends.

FIG. 6B shows the portion 400 after the link member 302 and end effector 402 have been rotated in the pitch direction about axis E as indicated in FIG. 5B. Similarly as shown in FIG. 6A, the flexure 320 has flexed and cables 410a-410d have bent to accommodate the rotated position.

Figure 7A:
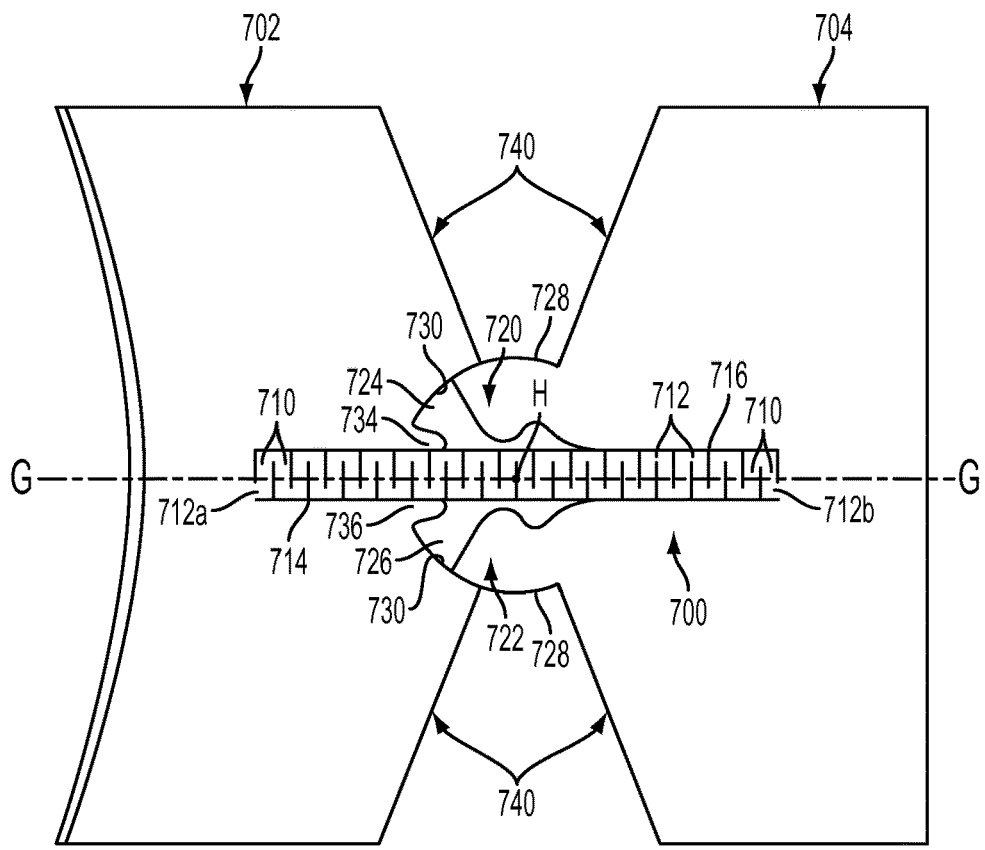
FIGS. 7A and 7B show views of an example flexure which can be used in the wrist mechanisms described herein.
Figure 7B:
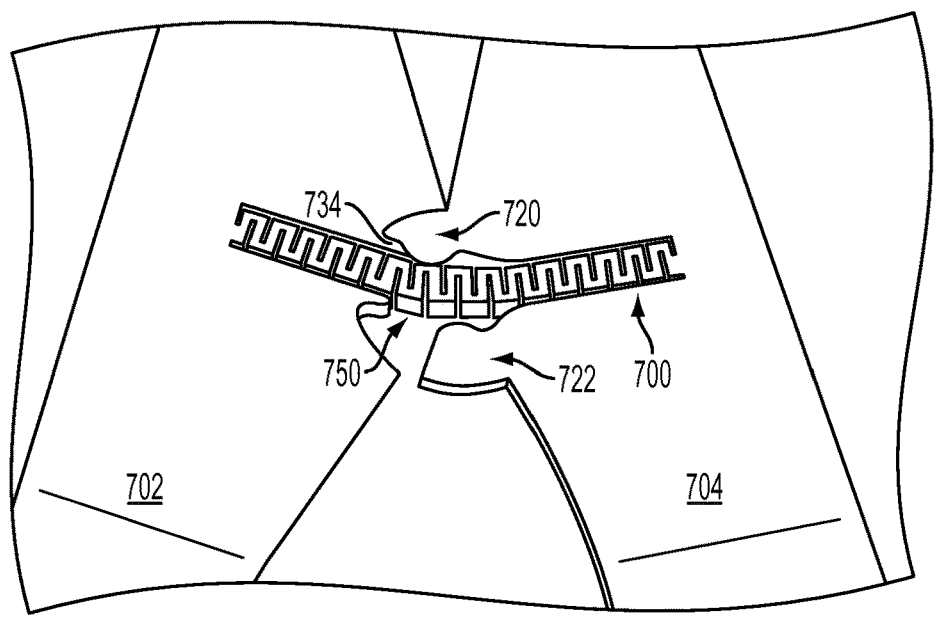

FIGS. 7A and 7B are views of an example implementation of a flexure 700 which can be used in the wrist mechanisms described herein. For example, flexure 700 can be used for any of flexures 320-326 of FIG. 4. Flexure 700 is connected between link members 702 and 704, which can, for example, be adjacent link members 302 and 304, or 304 and 306 as described above with reference to FIG. 4. A longitudinal axis G can be, for example, longitudinal axis D described above in particular examples. Flexure 700 allows rotational motion between link members 702 and 704 about axis H, which can be axis E or axis F as described above in some examples.

FIG. 7A shows flexure 700 in an unflexed state, where the link members 702 and 704 have central longitudinal axes aligned or approximately aligned along axis G similarly as shown in FIG. 4. In the example implementation shown, flexure 700 includes multiple linear segments 710 which are arranged parallel to each other in a lengthwise orientation in a dimension perpendicular or approximately perpendicular to the longitudinal axis G, where each segment has the same or approximately the same length. The segments 710 are connected to each other as a chain in an S-pattern or configuration such that opposite ends of each segment 710 are connected to different adjacent segments at or near the ends of the adjacent segments. In this example, the segments 710 can be connected by link segments 712 which are oriented parallel or approximately parallel to the axis G and join the ends of the segments 710. For example, the segments 710 and 712 can be formed from the unitary, single piece of material from which the link members 702 and 704 are formed, as described above, e.g., portions of the unitary piece are cut in an S-pattern to form the segments 710 and 712.

Each end of the flexure 700 can be connected to the associated link member 702 and 704 by the last link segment 712a and 712b of the flexure 700, respectively. This connection can be provided within a recess 714 in the end side of link member 702 and a recess 716 in the end side of link member 704, such that the connection points for a flexure are within a link member past the end side surfaces 740 of that link member. The recesses 714 and 716 allow the flexure 700 to be made of a longer length, which allows a greater number of link segments 710 and 712 to be used. This in turn can reduce the maximum amount of flex needed from any one of the segments 710 or 712 in a fully rotated position of the coupled link members. Other implementations can use flexures of different lengths, with a different number of number of segments and recesses 714 and/or 716 having different lengths than shown.

Stop members 720 and 722 can also be included in the wrist mechanism for use with the flexure 700. In this example, stop members 720 and 722 are positioned on opposite sides of flexure 700 and extend out from the end side of one of the link members, such as link member 704, toward the adjacent link member, such as link member 702. The stop members can be extensions of the associated link members and formed from the same unitary, single piece of material from which the link members 702 and 704 are formed, as described above.

The stop members 720 and 722 are aligned with recesses 724 and 726, respectively, in the opposing link member 702. One of the stop members engages its associated recess when the link members 702 and 704 are rotated with respect to each other, as described below for FIG. 7B. In the described implementation, the stop members 720 and 722 have curved outer sides 728 which are aligned with curved recess surfaces 730 of the opposing link member 702 such that the outer sides 728 move close to or slide against the curved surfaces 730. In some implementations, the outer sides 728 are positioned close to the curved surfaces 730 (e.g., 5-10 microns apart in a non-limiting example) but do not contact or slide against the surfaces 730 in rotated positions. In other implementations, the outer sides 728 contact and slide against the associated curved surfaces 730 in rotated positions. Either form of such engagement can help reduce or prevent torsional flex of the associated link members 702 and 704 about the axis G in some implementations, e.g., where the curved sides and surfaces may contact to prevent or reduce such torsional flex, and/or can help guide the rotation of the members based on the positions of the curved surfaces 728 and 730 of the stop member and its recess.

In addition, receiving members 734 and 736 can be attached to the link member 702 within the recesses 724 and 726, respectively. The receiving members 734 and 736 are positioned within the pathway of the stop members 720 and 722, respectively, to contact the leading edge of the associated stop member 720 and 722 and stop the movement of that stop member. Each stop member and receiving member thus limits the motion of the connected link members in one direction of the rotational degree of freedom about axis H. In other implementations, stop members and/or receiving members can also or alternatively be positioned at different locations of the wrist mechanism to similarly limit the motion in the rotational degree of freedom about axis H, such as on the end surfaces 740. For example, the stop and/or receiving members can be formed as part of the unitary piece of material forming the link members 702 and 704 and flexure 700, e.g., portions of the unitary piece cut to form the stop and/or receiving members.

FIG. 7B shows link members 702 and 704 and flexure 700 of FIG. 7A after the link members have been rotated about axis H in a rotational degree of freedom. As shown, flexure 700 has flexed to accommodate the motion, where segments 710 and 712 of the flexure have been changed in position and/or orientation relative to the unflexed neutral state shown in FIG. 7A. Segments 710 and 712 in the center portion 750 of the flexure 700 have been flexed more than segments located closer to the two ends of the flexure 700. The link members 702 and 704 have been rotated the maximum amount in the direction shown as allowed by the stop member 720, where the stop member 720 has engaged the receiving member 734.

In some implementations, the elements of the wrist mechanism such as link members and flexure segments can be modeled using finite element analysis to determine the length of the flexure 700, the dimensions and number of the segments 710 and 712, and how much the flexure is to be extended into the recesses 714 and 716 of link members 702 and 704 to obtain a desired range in the rotational degree of freedom and to obtain the desired amounts of flex in the segments of the flexure. The greater the number of segments 710, the less that each segment needs to individually flex and the less amount of flex needed at the center portion 750 of greatest flex. For example, some materials may have less ability to flex or may wear out from being flexed, and a greater number of segments 710 (e.g., of shorter width) can be used if the flexure is made of such a material. In the flexure implementation shown, the entire range of rotational motion in the degree of freedom is about 44 degrees. This range can be made greater or less in other implementations by changing the location, dimensions and/or shape of the stop members 720 and 720 and/or receiving members 734 and 736.

When moving the link members 702 and 704 in the rotational degree of freedom, the curved side of stop member 720 engages the corresponding side of its associated recess 724 in FIG. 7B. This engagement can help guide the rotational motion of the link members. In addition, this engagement can prevent or reduce undesired torsional flex of the link members 702 and 704 about longitudinal axis G since the surfaces of the engaged stop member 720 and recess 724 can contact and block or reduce that motion. This allows the link members 702 and 704 to be linked together by the flexures such as flexure 700 without needing additional connections, linkages, or tension for stability.

In some implementations, the curved surfaces 728 of stop members 720 and 722 and the associated recess surfaces 730 of the recesses 724 can be cut such that these surfaces are aligned toward the center of the cylindrical link members, e.g., approximately towards axis G. In other implementations, these surfaces can be cut in other orientations. For example, an off-axis cut can be made such that the surfaces 728 and 730 are parallel or approximately parallel to the longitudinal axis G. Some implementations can provide angled cuts of the surfaces such that the surfaces 728 and 730 are beveled with respect to the linear direction from the cut location toward the longitudinal axis G. Such off-axis and/or beveled side surfaces may in some implementations further reduce torsional deflections of the link members 702 and 704 with respect to each other about axis G, since the surfaces 728 and 730 may lock together more strongly with respect to those deflections when engaged with each other.

Figure 8:
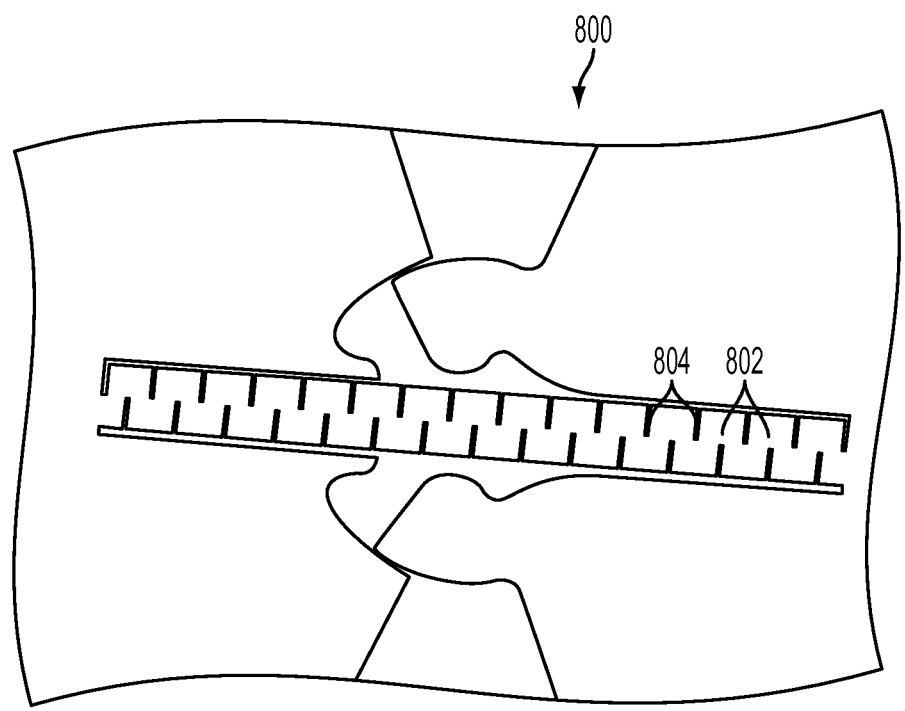
FIG. 8 is an example of another implementation of a flexure similar to the flexure of FIGS. 7A and 7B.

FIG. 8 is an example of another implementation of a flexure 800 similar to flexure 700 of FIGS. 7A and 7B. Flexure 800 is similarly configured in an S-configuration of segments 802. In this example, the segments 802 are separated by gaps 804 of smaller lengths than those shown in FIGS. 7A and 7B and have been precisely laser-cut in the wrist mechanism material.

Although the present embodiments have been described in accordance with the examples shown, one of ordinary skill in the art will readily recognize that there could be variations to the embodiments and those variations would be within the spirit and scope of the present disclosure. Accordingly, many modifications may be made by one of ordinary skill in the art without departing from the spirit and scope of the appended claims.

What is claimed is:

1. A surgical instrument comprising: an end effector and a unitary wrist mechanism coupled to the end effector; wherein the unitary wrist mechanism is formed from a single piece of material, provides one or more degrees of freedom to the end effector, and comprises a plurality of adjacent link members linked together in series, a flexure, and a stop member; wherein the plurality of adjacent link members comprises a first pair of adjacent link members; wherein the flexure comprises a chain of connected segments and connects the first pair of adjacent link members to enable rotational movement of the first pair of adjacent link members relative to each other to provide a degree of freedom of the one or more degrees of freedom to the end effector; and wherein the stop member is between the first pair of adjacent link members and prevents the rotational movement of the first pair of adjacent link members relative to each other beyond a predetermined angular range.

2. The surgical instrument of claim 1, wherein: each of the plurality of adjacent link members is annular and is cylindrical or approximately cylindrical.

3. The surgical instrument of claim 1, wherein: each of the first pair of adjacent link members has a longitudinal axis; and each longitudinal axis is aligned or approximately aligned in an unflexed state of the flexure.

4. The surgical instrument of claim 1, wherein: the unitary wrist mechanism comprises a first end and a second end opposite the first end, and a longitudinal axis of the unitary wrist mechanism is defined by the first and second ends; the unitary wrist mechanism provides at least two degrees of freedom to the end effector; the at least two degrees of freedom comprise a first degree of freedom about a pitch axis and a second degree of freedom about a yaw axis; and the yaw axis is nonparallel to the pitch axis and is nonparallel to the longitudinal axis of the unitary wrist mechanism.

5. The surgical instrument of claim 1 wherein:
the first pair of adjacent link members comprises a first adjacent link member and a second adjacent link member;
the first adjacent link member comprises an end side;

the second adjacent link member comprises an end side opposing the end side of the first adjacent link member; and the flexure is coupled between the end sides of the first and second adjacent link members.

6. The surgical instrument of claim 1, wherein:

the first pair of adjacent link members comprises a first adjacent link member and a second adjacent link member;

a longitudinal axis is defined for each of the first and second adjacent link members;

a rotational axis is defined perpendicular or approximately perpendicular to at least one of the longitudinal axes of the first and second adjacent link members; and the rotational movement of the first pair of adjacent link members relative to each other is about the rotational axis.

7. The surgical instrument of claim 1, wherein:

the connected segments are linear segments connected in an S-pattern.

8. The surgical instrument of claim 1, wherein:

the first pair of adjacent link members comprises a first adjacent link member and a second adjacent link member;

the first adjacent link member comprises a tapered end portion tapered to allow the rotational movement of the first pair of adjacent link members relative to each other; and the second adjacent link member comprises a tapered end portion tapered to allow the rotational movement of the first pair of adjacent link members relative to each other.

9. The surgical instrument of claim 1, wherein: the flexure when displaced from a neutral position provides a spring force to the first pair of adjacent link members connected by the flexure.

10. The surgical instrument of claim 1, wherein:

the first pair of adjacent link members comprises a first adjacent link member and a second adjacent link member;

the first adjacent link member comprises the stop member; and the second adjacent link member comprises a receiving recess in which the stop member is engaged when the first pair of adjacent link members is rotated by a predetermined amount with respect to each other.

11. The surgical instrument of claim 1, wherein: the surgical instrument comprises a tube and a shaft; the shaft is coupled to the unitary wrist mechanism; the tube extends through the shaft, through the unitary wrist mechanism, and to the end effector; and the tube is operative to provide a passage for material to be moved to or from the end effector.

12. The surgical instrument of claim 1, wherein: the unitary wrist mechanism comprises a second flexure; and the second flexure connects the first pair of adjacent link members.

13. The surgical instrument of claim 12, wherein:

the first pair of adjacent link members comprises a first adjacent link member and a second adjacent link member;

a longitudinal axis of the first pair of adjacent link members is defined through the first and second adjacent link members; and the flexure and the second flexure are on opposite or approximately opposite sides of the longitudinal axis of the first pair of adjacent link members.

14. The surgical instrument of claim 1, wherein: the surgical instrument comprises a force transmission element and an actuator; and the force transmission element is coupled to the unitary wrist mechanism via the actuator to enable active moving of the end effector by rotating at least one link member of the plurality of adjacent link members in at least one of the one or more degrees of freedom.

15. The surgical instrument of claim 14, wherein:

the force transmission element comprises one or more cables.

16. A wrist mechanism for a surgical instrument, the wrist mechanism comprising: a plurality of adjacent link members linked together; and one or more flexures each comprising a chain of connected segments; wherein each flexure of the one or more flexures connects a pair of adjacent link members of the plurality of adjacent link members to enable rotational movement of the pair of adjacent link members relative to each other to provide an associated degree of freedom to an end effector coupled to the wrist mechanism; wherein the connected segments are entirely linear segments connected in an S-pattern; wherein the plurality of adjacent link members and the one or more flexures are formed from a single piece of material; wherein the wrist mechanism comprises a first end and a second end opposite the first end; and wherein the wrist mechanism provides at least one degree of freedom between the first and second ends of the wrist mechanism.

17. The wrist mechanism of claim 16, wherein: each of the plurality of adjacent link members is annular and is cylindrical or approximately cylindrical; a longitudinal axis of the wrist mechanism is defined through the plurality of adjacent link members; and each flexure of the one or more flexures couples the pair of adjacent link members to enable the rotational movement of the pair of adjacent link members relative to each other about a rotational axis extending perpendicular or approximately perpendicular to the longitudinal axis of the wrist mechanism.

18. The wrist mechanism of claim 16, wherein: the wrist mechanism comprises a stop member coupled to a first link member of the plurality of adjacent link members and coupled between the plurality of adjacent link members; and the stop member is configured to engage an associated receiving recess in an opposing side end of a second link member of the plurality of adjacent link members in response to the plurality of adjacent link members being rotated by a predetermined amount with respect to each other.

19. A wrist mechanism for a surgical instrument, the wrist mechanism comprising: a first link member, a second link member adjacent the first link member, and a flexure between the first and second link members; wherein the flexure connects the first and second link members to enable rotational movement of the first and second link members relative to each other to provide an associated degree of freedom to an end effector coupled to the wrist mechanism; wherein the first link member comprises a stop member, the second link member comprises a receiving member, and the stop member and the receiving member are positioned such that the stop member contacts the receiving member to prevent the rotational movement of the first and second link members relative to each other beyond a predetermined angular range; and wherein the first and second link members, the flexure, the stop member, and the receiving member are formed from a single piece of material.

* * * * *